United States Patent [19]
Wang et al.

[11] Patent Number: 4,892,925
[45] Date of Patent: Jan. 9, 1990

[54] PROCESS FOR PREPARING PHENOLIC HYDROXYL-CONTAINING COMPOUNDS FROM 2,6-DIBROMO-3,5-DIALKYL-4-HYDROXY-BENZYL ETHERS

[75] Inventors: Chun S. Wang, Lake Jackson, Tex.; Abel Mendoza, Midland, Mich.; David B. Fritz, Lake Jackson, Tex.

[73] Assignee: The Dow Chemical Company, Midland, Mich.

[21] Appl. No.: 300,460

[22] Filed: Jan. 23, 1989

[51] Int. Cl.$^4$ ............................................. C08G 65/38
[52] U.S. Cl. .................................... 528/219; 528/102; 528/103; 525/524; 525/390
[58] Field of Search .......................... 528/219; 525/390

[56] References Cited
U.S. PATENT DOCUMENTS 3,989,531 11/1976 Orlando et al. ................. 106/15 FP
4,170,711 10/1979 Orlando et al. ..................... 568/610
4,727,119 2/1988 Berman et al. ...................... 525/482
4,731,423 3/1988 Mendoza et al. .................... 525/480
4,783,363 11/1988 Berman et al. ...................... 428/285

FOREIGN PATENT DOCUMENTS 0742755 9/1966 Canada ............................... 525/524
239784 10/1987 European Pat. Off. .

OTHER PUBLICATIONS

K. Auwers and F. A. Traun, "Dibromo–p–hydroxymesityl Alcohol", Chem. Berichte, vol. 32, pp. 3309–3317 (1899).

Primary Examiner—Lewis T. Jacobs
Assistant Examiner—Roberet E. L. Sellers, II

[57] ABSTRACT 2,6-dibromo-3,5-dialkyl-4-hydroxybenzyl ethers, glycidyl ethers thereof and reaction products with phenolic hydroxyl-containing compounds, and glycidyl ethers of the resulting new phenolic hydroxyl-containing compounds.

8 Claims, No Drawings

PROCESS FOR PREPARING PHENOLIC HYDROXYL-CONTAINING COMPOUNDS FROM 2,6-DIBROMO-3,5-DIALKYL-4-HYDROXYBENZYL ETHERS

FIELD OF THE INVENTION

The present invention concerns derivatives of 2,6-dibromo-3,5-dialkyl-4-hydroxybenzyl ether such as epoxy resins prepared therefrom and other reaction products of 2,6-dibromo-3,5-dialkyl-4-hydroxybenzyl ethers. The invention also concerns cured products thereof.

BACKGROUND OF THE INVENTION

One of the most frequent failures encountered in encapsulated micro devices is the so-called open circuit which results from a break of the bonding wire between the circuitry. The breakage is primarily due to corrosion. This corrosion is initiated by the impurities in epoxy resins, such as halogen, which upon exposure to heat and moisture generate a corrosive acid.

Since the introduction of the low chloride epoxy resins, the wire bond failure due to the chloride impurities in the resin has become much less prominent than that due to the bromine from the fire retardant in the encapsulation formulation. Water extracts of molding compounds after high temperature storage have been found to contain bromide ion levels directly proportional to the bromine content in the molding compounds. A direct relationship between failure rate and bromine content in the molding compound has also been established.

It would therefore, be desirable to have available epoxy resins which when employed in curable formulations would have good thermal and hydrolytic stability to the molding formulation while providing fire retardancy properties.

SUMMARY OF THE INVENTION

One aspect of the present invention pertains to the diglycidyl ether of 2,6-dibromo-3,5-dialkyl-4-hydroxybenzyl ethers or a mixture of any two or more of such diglycidyl ethers.

Another aspect of the present invention pertains to an advanced epoxy resin prepared by reacting one or more diglycidyl ethers or polyglycidyl ethers of a di- or polyhydric phenol with one or more of the 2,6-dibromo-3,5-dialkyl-4-hydroxybenzyl ethers.

Another aspect of the present invention pertains to an advanced epoxy resin prepared by reacting a di- or polyhydric phenol with one or more of the diglycidyl ethers of 2,6-dibromo-3,5-dialkyl-4-hydroxybenzyl ethers.

Another aspect of the present invention pertains to a process for preparing phenolic hydroxyl-containing compounds represented by the formulas VII, VIII, IX, X or XI

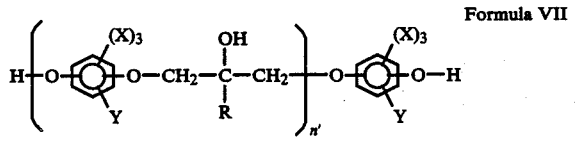
Formula VII

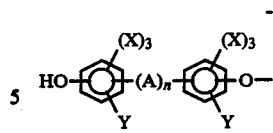
Formula VIII

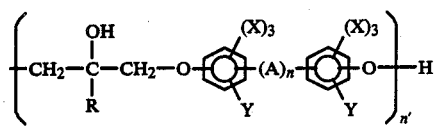
Formula IX

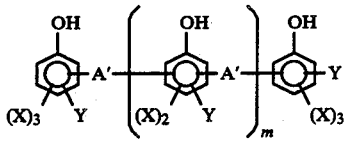
Formula X

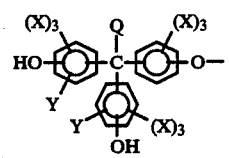

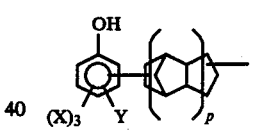
Formula XI

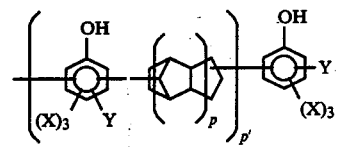

wherein each A is independently a divalent hydrocarbyl group having from 1 to about 12 carbon atoms; each A' is independently a divalent hydrocarbyl group having from 1 to about 10 carbon atoms; each Q is independently hydrogen or an alkyl group having from 1 to about 4 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms or a halogen atom; each Y is independently hydrogen or a group represented by the following formula XII wherein R' is an alkyl group having from 1 to about 6 carbon atoms with the proviso that at least one Y group is a group represented by formula XII;

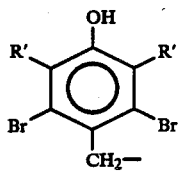

Formula XII m has an average value from about 0.01 to about 8; m' has an average value from zero to about 10; n has a value of zero or 1; n' has an average value from about zero to about 3; each p has a value from zero to about 10; and each p' has an average value from zero to about 8; which process comprises reacting one or more 2,6-dibromo-3,5-dialkyl-4-hydroxybenzyl ethers with one or more phenolic hydroxyl containing compounds having an average of more than one phenolic hydroxyl group per molecule.

Another aspect of the present invention pertains to mixtures of epoxy resins comprising (A) one or more diglycidyl ethers of 2,6-dibromo-3,5-dialkyl-4-hydroxybenzyl ether and (B) one or more epoxy resins having an average of more than one vicinal epoxide groups per molecule.

Another aspect of the present invention pertains to curable compositions comprising one or more diglycidyl ethers of 2,6-dibromo-3,5-dialkyl-4-hydroxybenzyl ethers and a curing amount of one or more suitable curing agents or curing catalysts and the products resulting from curing such curable compositions.

Another aspect of the present invention pertains to curable compositions comprising mixtures of at least one diglycidyl ether of a 2,6-dibromo-3,5-dialkyl-4-hydroxybenzyl ether and at least one different epoxy resin having an average of more than one vicinal epoxide group per molecule and a curing amount of one or more suitable curing agents or curing catalysts therefor as well as the products resulting from curing such curable compositions.

Another aspect of the present invention pertains to the products resulting from curing the epoxy resins prepared by reacting the product resulting from reacting one or more 2,6-dibromo-3,5-dialkyl-4-hydroxybenzyl ethers with one or more phenolic hydroxyl containing compounds having an average of more than one phenolic hydroxyl group per molecule with an epihalohydrin and converting the intermediate halohydrin product to the glycidyl ether with one or more suitable curing agents.

DETAILED DESCRIPTION OF THE INVENTION

The 2,6-dibromo-3,5-dialkyl-4-hydroxybenzyl ethers can be prepared by hydrolyzing 4-bromomethyl-3,5-dibromo-2,6-dialkylphenol with water in the presence of one or more suitable solvent(s) at a temperature suitably from about 30° C. to about 100° C., more suitably from about 45° C. to about 90° C., most suitably from about 60° C. to about 70° C. for a time sufficient to complete the reaction, suitably from about 1 to about 10, more suitably from about 2 to about 8, most suitably from about 3 to about 6 hours. The lower temperatures require longer reaction times whereas the higher temperatures require shorter reaction times. At temperatures below about 50° C., the reaction is slow. At temperatures above about 70° C., a pressure vessel is required since the most preferred solvent system (acetone-water) mixture boils below 70° C.

The reactants are suitably employed in quantities which provide a weight ratio of water to 4-bromomethyl-3,5-dibromo-2,6-dialkylphenol suitably from about 0.1:1 to about 1:1, more suitably from about 0.2:1 to about 0.8:1, most suitably from about 0.5:1 to about 0.7:1. At ratios below about 0.1:1, the reaction is very slow. At ratios above about 1:1, the main product is 3,5-dibromo-4-hydroxymethyl-2,6-dialkyl phenol rather than the desired 2,6-dibromo-3,5-dialkyl-4-hydroxybenzyl ether.

Suitable solvents which can be employed in the preparation of 2,6-dibromo-3,5-dialkyl-4-hydroxybenzyl ether include, for example, aliphatic ketones, aliphatic carboxylic acids, polar aprotic solvents, ethers, glycol ethers, water, combinations thereof and the like. Particularly suitable such solvents include, for example, acetone, methyl ethyl ketone, methyl isobutyl ketone, cyclohexanone, acetic acid, dimethyl formamide, dimethyl acetamide, dimethyl sulfoxide, N-methylpyrrolidone, 2-methoxyethyl acetate, ethylene glycol dimethyl ether, dioxane, tetrahydrofuran, combinations thereof and the like.

The 2,6-dibromo-3,5-dialkyl-4-hydroxybenzyl ethers employed in the present invention can be represented by the following formula I

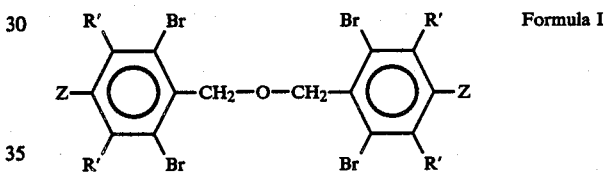

Formula I wherein each R' is independently an alkyl group having from 1 to about 10, more suitably from 1 to about 6, most suitably from 1 to about 3 carbon atoms and each Z is a hydroxyl group.

The diglycidyl ethers of 2,6-dibromo-3,5-dialkyl-4-hydroxybenzyl ethers can be prepared by reacting the corresponding 2,6-dibromo-3,5-dialkyl-4-hydroxybenzyl ethers with an excess of an epihalohydrin such as, for example, epichlorohydrin, epibromohydrin or epiiodohydrin or lower alkyl derivatives thereof in the presence of a suitable catalyst and dehydrohalogenating the resulting halohydrin product with a basic acting compound. Suitable methods are more fully disclosed by Wang et al. in U.S. Pat. No. 4,585,838, by Chang et al. in U.S. Pat. No. 4,582,892, by Wang et al. in U.S. Pat. No. 4,499,255, and by Wang et al. in allowed U.S. application Ser. No. 85,035 filed August 13, 1987, all of which are incorporated herein by reference in their entirety.

The diglycidyl ethers of 2,6-dibromo-3,5-dialkyl-4-hydroxybenzyl ethers can be represented by the aforementioned formula I wherein each Z is a glycidyl ether group represented by the following formula XIX

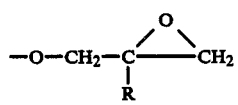

Formula XIX wherein each R is independently hydrogen or a lower alkyl group having from 1 to about 3 carbon atoms.

The advanced epoxy resins of the present invention can be prepared by reacting the epoxy resin with the phenolic hydroxyl-containing compound. The advanced product can be terminated in either an epoxy group or a phenolic hydroxyl group depending upon the ratio in which the reactants are employed. The reactants can be employed in quantities which provide a ratio of phenolic hydroxyl groups per epoxy group suitably from about 0.1:1 to about 1.2:1, more suitably from about 0.1:1 to about 0.6:1, most suitably from about 0.1:1 to about 0.2:1. The products produced when the reaction mixture contains an excess of the phenolic hydroxyl-containing compound are predominantly those which are terminated in a phenolic hydroxyl group. The products produced when the reaction mixture contains an excess of the epoxy-containing compound are predominantly those which are terminated in an epoxy group. Of course, in either event, mixtures of products are actually produced.

One or more of the diglycidyl ethers of 2,6-dibromo-3,5-dimethyl-4-hydroxybenzyl ethers can be mixed with one or more other epoxy resin which are different from the diglycidyl ethers of 2,6-dibromo-3,5-dimethyl-4-hydroxybenzyl ethers. The mixture can contain suitably from about 1 to about 99, more suitably from about 5 to about 50, most suitably from about 10 to about 25, percent by weight of the diglycidyl ethers of 2,6-dibromo-3,5-dimethyl-4-hydroxybenzyl ethers and suitably from about 99 to about 1, more suitably from about 95 to about 50, most suitably from about 90 to about 75 percent by weight of the other epoxy resin(s); the weights being based upon the combined weight of all of the epoxy resins present in the mixture.

Suitable epoxy resins which can be blended with the diglycidyl ethers of 2,6-dibromo-3,5-dimethyl-4-hydroxybenzyl ethers include, for example, the di- or polyglycidyl ethers of a compound having two or more aliphatic or aromatic hydroxyl groups per molecule, such as dihydric phenols, alkyl or alkoxy or halogen substituted dihydric phenols, bisphenols, alkyl or alkoxy or halogen substituted bisphenols, trisphenols, alkyl or alkoxy or halogen substituted trisphenols, phenol-aldehyde novolac resins, alkyl or alkoxy or halogen substituted phenol-aldehyde novolac resins, glycols, polyglycols, reaction products of an alkylene oxide such as ethylene oxide, propylene oxide or butylene oxide with a compound containing two or more aromatic hydroxyl groups per molecule, combinations thereof and the like. Particularly suitable epoxy resins which can be blended with the diglycidyl ethers of 2,6-dibromo-3,5-dimethyl-4-hydroxybenzyl ethers include, for example, those epoxy resins described by Hefner, Jr. in U.S. Pat. No. 4,668,745 and by Wang et al. in U.S. Pat. No. 4,684,701, both of which are incorporated herein in their entirety. Most particularly suitable for blending are the diglycidyl ethers of resorcinol, hydroquinone, catechol, dihydroxybiphenyl, bisphenol A, bisphenol F, bisphenol K, bisphenol S and the polyglycidyl ethers of phenolformaldehyde novolac resins, cresol-formaldehyde novolac resins, combinations thereof and the like. Also particularly suitable are the halogenated, particularly the brominated derivatives of the diglycidyl ethers and polyglycidyl ethers enumerated above.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate.acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate.acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference in their entirety.

The amount of advancement catalyst depends, of course, upon the particular reactants and catalyst employed; however, the catalyst is usually employed in quantities of from about 0.03 to about 3, preferably from about 0.3 to about 1.5, most preferably from about 0.05 to about 1.5 percent by weight based upon the weight of the epoxy-containing compound. The catalyst can, if desired, be employed in a solvent.

If desired, the advancement reaction can be conducted in the presence of a solvent. Suitable such solvents include, for example, alcohols, ketones, glycol ethers, aliphatic and aromatic hydrocarbons, halogenated aliphatic hydrocarbons, glycols, polyglycols, cyclic or acyclic ethers, combinations thereof and the like. Particularly suitably such solvents include, methanol, ethanol, isopropanol, acetone methyl ethyl ketone, methyl isobutyl ketone, hexane, heptane, octane, nonane, decane, benzene, toluene, xylene, propylene glycol methyl ether, dipropylene glycol methyl ether, ethylene glycol n-butyl ether, propanol, n-butanol, polyoxyethylene glycol, dioxane, combinations thereof and the like.

The reaction products of 2,6-dibromo-3,5-dialkyl-4-hydroxybenzyl ether and a phenolic hydroxyl-containing compound, are prepared by conducting the reaction at a temperature suitably from about 50° C. to about 150° C., more suitably from about 60° C. to about 120° C., most suitably from about 70° C. to about 90° C. for a time sufficient to complete the reaction, suitably from about 2 to about 12, more suitably from about 3 to about 10 most suitably from about 4 to about 8 hours. The lower temperatures require longer reaction times whereas the higher temperatures require shorter reaction times. At temperatures below about 50° C., the reaction proceeds very slowly. At temperatures above about 150° C., splitting of 2,6-dimethyl-3,5-dibromophenol will occur.

The reactants are suitably employed in quantities which provide a ratio phenolic hydroxyl groups from 2,6-dibromo-3,5-dialkyl-4-hydroxybenzyl ether to aromatic rings from the phenolic hydroxyl-containing compound suitably from about 0.05:1 to about 0.5:1, more suitably from about 0.05:1 to about 0.3:1, most suitably from about 0.05:1 to about 0.2:1. At ratios below about 0.05:1, there is not enough bromine introduced into the system to achieve fire retardancy. At ratios above about 0.5:1, a very high molecular weight product will form.

The 2,6-dibromo-3,5-dialkyl-4-hydroxybenzyl ether can be reacted with any phenolic hydroxyl-containing compound having an average of more than one phenolic hydroxyl group per molecule. Suitable such phenolic compounds include, for example, dihydroxy benzene, bisphenols, phenol-aldehyde novolac resins, substituted phenol-aldehyde novolac resins, unsaturated hydrocarbon-phenol resins, unsaturated hydrocarbon-substituted phenol resins, combinations thereof and the like. Particularly suitable such phenolic hydroxyl-containing compounds which can be reacted with the 2,6-dibromo-3,5-dialkyl-4-hydroxybenzyl ether include those represented by the following formulas II, III, IV, V or VI each R is independently hydrogen or an alkyl group having from 1 to about 3 carbon atoms; each X is independently hydrogen, a hydrocarbyl or hydrocarbyloxy group having suitably from 1 to about 12, more suitably from 1 to about 6, most suitably from 1 to about 4, carbon atoms or a halogen atom, preferably chlorine or bromine; m has an average value suitably from about 0.01 to about 8, more suitably from about 1 to about 6, most suitably from about 2 to about 4; m' has an average value suitably from zero to about 10, more suitably from zero to about 6, most suitably from zero to about 3 n has a value of zero or 1; n' has an average value suitably from zero to about 3, more suitably from zero to about 2, most suitably from zero to about 1; each p suitably has a value from zero to about 10, more suitably from zero

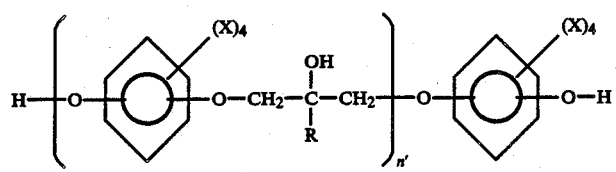

Formula II

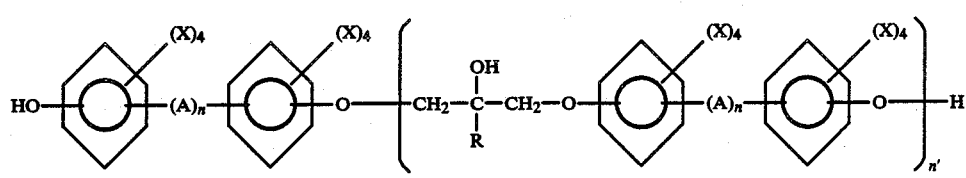

Formula III

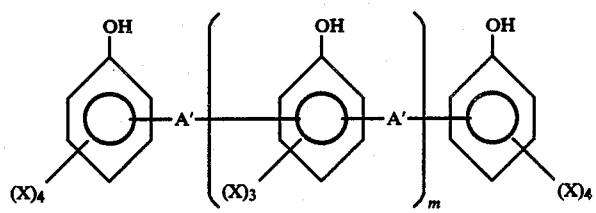

Formula IV

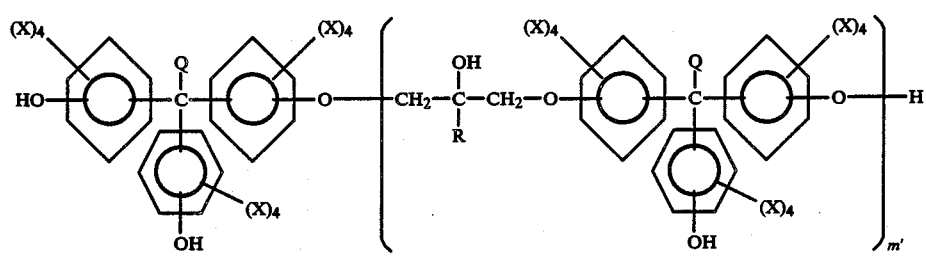

Formula V

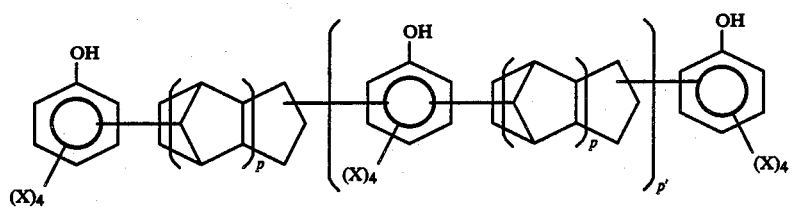

Formula VI wherein each A is independently a divalent hydrocarbyl group having suitably from 1 to about 12, more suitably from 1 to about 6, most suitably from 1 to about 4, carbon atoms; each A' is independently a divalent hydrocarbyl group having from 1 to about 10, more suitably from 1 to about 4, most suitably from 1 to about 2, carbon atoms; each Q is independently hydrogen or an alkyl group having from 1 to about 4 carbon atoms;

to about 6, most suitably from zero to about 3; and each p' suitably has an average value from zero to about 8, more suitably from about 1 to about 6, most suitably from about 2 to about 4.

The term hydrocarbyl as employed herein means any aliphatic, cycloaliphatic, aromatic, aryl substituted aliphatic or cycloaliphatic, or aliphatic or cycloaliphatic substituted aromatic groups. Likewise, the term hydrocarbyloxy means a hydrocarbyl group having an oxygen linkage between it and the element to which it is attached. The term divalent hydrocarbyl group refers to the aforementioned hydrocarbyl groups minus an additional hydrogen atom.

The diglycidyl ether of 2,6-dibromo-3,5-dialkyl-4-hydroxybenzyl ether can, if desired, be blended with other epoxy resins such as those which are represented by the aforementioned formulas II-VI wherein the aromatic hydroxyl groups have been replaced with glycidyl ether groups.

The reaction products of 2,6-dibromo-3,5-dialkyl-4-hydroxybenzyl ether with the phenolic hydroxyl-containing compounds can be represented by the following formulas VII, VIII, IX, X and XI

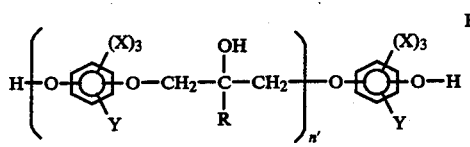

Formula VII

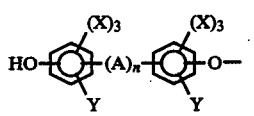

Formula VIII

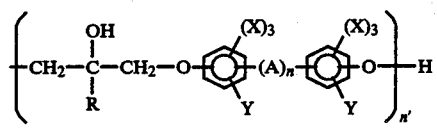

Formula IX

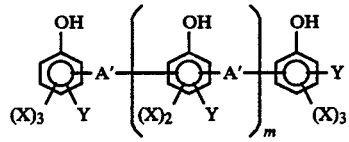

Formula X

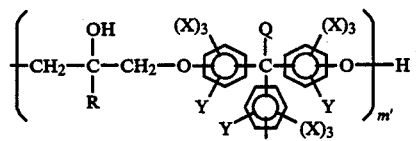

Formula XI

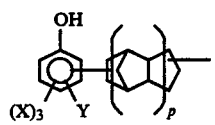

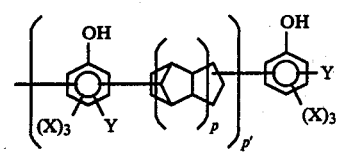

wherein each A is, independently a divalent hydrocarbyl group having suitably from 1 to about 12, more suitably from 1 to about 6, most suitably from 1 to about 4, carbon atoms; each A' is independently a divalent hydrocarbyl group having from 1 to about 10, more suitably from 1 to about 4, most suitably from 1 to about 2, carbon atoms; each Q is independently hydrogen or an alkyl group having from 1 to about 4 carbon atoms; each R is independently hydrogen or an alkyl group having from 1 to about 3 carbon atoms; each X is independently hydrogen, a hydrocarbyl or hydrocarbyloxy group having suitably from 1 to about 12, more suitably from 1 to about 6, most suitably from 1 to about 4, carbon atoms or a halogen atom, preferably chlorine or bromine; each Y is independently hydrogen or a group represented by the following formula XI wherein R' is an alkyl group having from 1 to about 10, preferably from 1 to about 5, most preferably from 1 to about 3, carbon atoms with the proviso that at least one Y group is a group represented by formula XII;

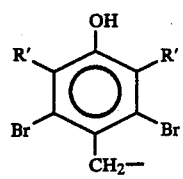

Formula XII m has an average value suitably from about 0.01 to about 8, more suitably from about 1 to about 6, most suitably from about 2 to about 4; m' has an average value suitably from zero to about 10, more suitably from zero to about 6, most suitably from zero to about 3; n has a value of zero or 1; n' has an average value from about zero to about 3, more suitably from about zero to about 2, most suitably from azero to about 1; each p suitably has a value from zero to about 10, more suitably from zero to about 6, most suitably from zero to about 3; and each p' suitably has an average value from zero to about 8, more suitably from about 1 to about 6, most suitably from about 2 to about 4.

The epoxy resins prepared by reacting the product resulting from reacting the 2,6-dibromo-3,5-dialkyl-4-hydroxybenzyl ethers with phenolic hydroxyl containing compounds having an average of more than one phenolic hydroxyl group per molecule with an epihalohydrin and converting the intermediate halohydrin product to the glycidyl ether can be represented by the following formulas XIII, XIV, XV, XVI and XVII.

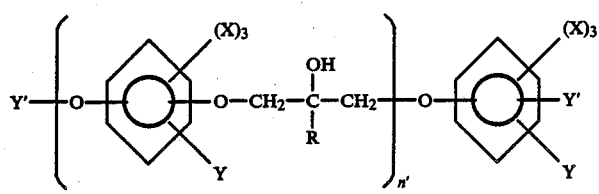

Formula XIII

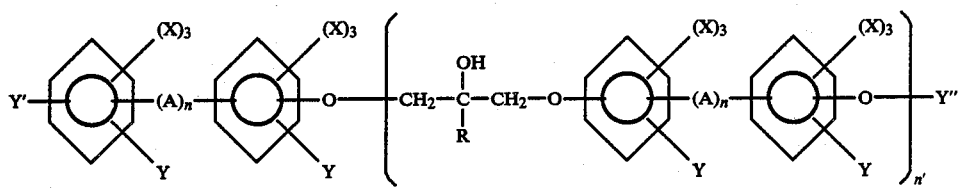

Formula XIV

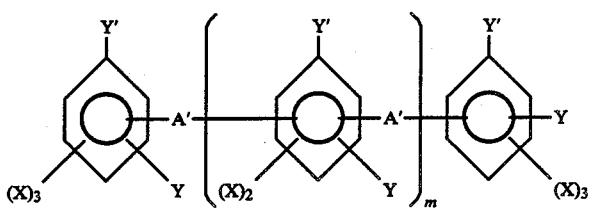

Formula XV

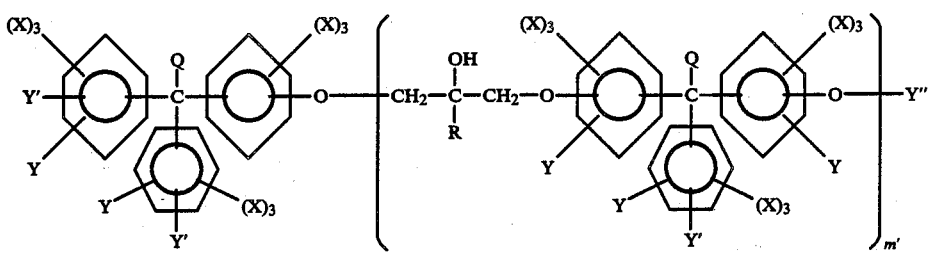

Formula XVI

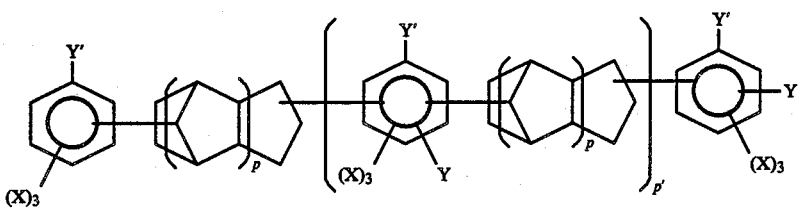

Formula XVII wherein each A is independently a divalent hydrocarbyl group having suitably from 1 to about 12, more suitably from 1 to about 6, most suitably from 1 to about 4, carbon atoms; each A' is independently a divalent hydrocarbyl group having from 1 to about 10, more suitably from 1 to about 4, most suitably from 1 to about 2, carbon atoms; each Q is independently hydrogen or an alkyl group having from 1 to about 4 carbon atoms; each R is independently hydrogen or an alkyl group having from 1 to about 3 carbon atoms; each X is independently hydrogen, a hydrocarbyl or hydrocarbyloxy group having suitably from 1 to about 12, more suitably from 1 to about 6, most suitably from 1 to about 4, carbon atoms or a halogen atom, preferably chlorine or bromine; each Y is independently hydrogen or a group represented by the following formula XVIII wherein each R' is an alkyl group having from 1 to about 10, preferably from 1 to about 5, more preferably from 1 to about 3 carbon atoms with the proviso that at least one Y group is a group represented by formula XVIII;

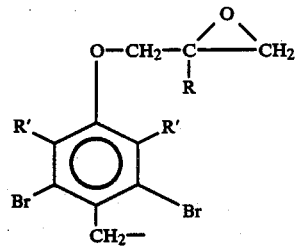

Formula XVIII each Y' is represented by the following formula XIX;

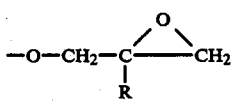

Formula XIX each Y" is represented by the following formula XX;

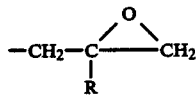

Formula XX m has an average value suitably from about 0.01 to about 8, more suitably from about 1 to about 6, most suitably from about 2 to about 4; m' has an average value suitably from zero to about 10, more suitably from zero to about 6, most suitably from zero to about 3; n has a value of zero or 1; n' has an average value suitably from zero to about 3, more suitably from zero to about 2, most suitably from zero to about 1; each p suitably has a value from zero to about 10, more suitably from zero to about 3, most suitably from zero to about 3; and each p' suitably has an average value from zero to about 8, more suitably from about 1 to about 6, most suitably from about 2 to about 4.

The epoxy resins of the present invention can be cured with any suitable curing agent for epoxy resins including, for example, primary and secondary aliphatic and aromatic polyamines, carboxylic acids and anhydrides thereof, phenolic hydroxyl-containing compounds having an average of two or more phenolic hydroxyl groups per molecule, guanidines, biguanides, urea-aldehyde resins, melamine-aldehyde resins, alkoxylated urea-aldehyde resins, alkoxylated melamine-aldehyde resins, phenol- or substituted phenol-aldehyde novolac resins, combinations thereof and the like. Particularly suitable curing agents include, for example, bis-(4-aminophenyl)sulfone, dicyandiamide, m-phenylenediamine, bis-(4-aminophenyl)methane, phthalic anhydride, maleic anhydride, phenol-formaldehyde novolac resins, cresol-formaldehyde novolac resins, combinations thereof and the like. The curing agents are employed in an amount which will effectively cure the composition containing the epoxy resin. These amounts will depend upon the particular modified epoxy resin and curing agent employed; however, suitable amounts include, for example, from about 0.0001 to about 1, more suitably from about 0.001 to about 1, most suitably from about 0.01 to about 1 equivalents of curing agent per epoxide equivalent for those curing agents which cure by reacting with the epoxy group of the epoxy resin or per hydroxyl group for those curing agents which cure by reacting with the aliphatic hydroxyl groups along the backbone of the epoxy resin. The *Handbook of Epoxy Resins* by Lee and Neville, McGraw-Hill, 1967 contains various discussions concerning the curing of epoxy resins as well as compilation of suitable curing agents. This handbook is incorporated herein by reference in its entirety.

The epoxy resins of the present invention can be blended with other materials such as solvents or diluents, fillers, pigments, dyes, flow modifiers, thickeners, reinforcing agents, wetting agents, leveling agents, flame retardant agents, plasticizers, mold releasing agents, extenders These additives are added in functionally equivalent amounts e.g., the pigments and/or dyes are added in quantities which will provide the composition with the desired color; however, they are suitably employed in amounts of from about 0.1 to about 10, more suitably from about 0.1 to about 1, most suitably from about 0.2 to about 0.5 percent by weight based upon the weight of the total formulation. The total formulation consists of epoxy resin(s), curing agent(s), filler(s), pigment(s), accelerator(s) and additives.

The modifiers such as thickeners, flow modifiers and the like can be suitably employed in amounts of from about 0.1 to about 10, more suitably from about 0.1 to about 1, most suitably from about 0.1 to about 0.5 percent by weight based upon the weight of the total formulation.

The fillers can be employed in amounts suitably from about 1 to about 95, more suitably from about 10 to about 90, most suitably from about 50 to about 80 percent by weight based upon the weight of the total formulation.

In addition to being employed to prepare epoxy resins therefrom, the meta halogenated phenolic hydroxyl-containing compositions of the present invention can be employed to cure the epoxy resins of the present invention or other epoxy resins or combinations thereof.

The epoxy resins of the present invention can be employed in the preparation of compositions suitable for such applications as coatings, castings, moldings, encapsulants, laminates, composites, potting compounds, and the like.

EXAMPLE 1

Preparation of 2,6-dibromo-3,5-dimethyl-4-hydroxybenzyl ether

A 373 g (1.0 mole) portion of 4-bromomethyl-3,5-dibromo-2,6-dimethylphenol is dissolved in 750 ml of acetone. The solution is heated to reflux and 250 ml of water is added. A clear solution is obtained. The solution is refluxed for five hours. A white precipitate forms during the refluxing period. The hot slurry is filtered to afford 184 g of white solid containing 97% ether and 3% 3,5-dibromo-2,6-dimethyl-4-hydroxymethylphenol by liquid chromatography. The solid is further purified by slurrying in 800 ml of acetone and 200 ml of water and refluxing for one-half hour. Hot filtration of the slurry produces a solid of 98+% purity with a melting point of 240°–241° C. The proton nuclear magnetic resonance spectrum has the following signals: (*DMSO d6) $\delta$;2.26 (s, 6H), 4.75 (s, 2H).

EXAMPLE 2

Alkylation and Epoxidation of Cresol Formaldehyde Novolac Resin

A. Alkylation

To a one-liter reaction vessel equipped with temperature control and indicating means and reflux condenser, are added 292.6 g (2.52 eq.) of cresol formaldehyde novolac resin (softening point=94.3° C. and average phenolic hydroxyl functionality=5), 65.4 g (0.217 eq.) of 2,6-dibromo-3,5-dimethyl-4-hydroxybenzyl ether and 80 g of methyl ethyl ketone. Upon stirring at room temperature and atmospheric pressure to thoroughly mix the contents, the temperature is raised to 80° C. and 2.0 g of p-toluenesulfonic acid is added as a catalyst. The mixture is allowed to stir at 80° C. until the slurry reaction mixture turns clear indicating all 2,6-dibromo-3,5-dimethyl-4-hydroxylbenzyl ether is reacted.

B. Epoxidation

To a 5-liter reaction vessel which is equipped with temperature and pressure control and indicating means, a means for the continuous addition of aqueous sodium hydroxide, a means for condensing and separating water from a codistillate mixture of water, solvent and epichlorohydrin and means for returning the solvent and epichlorohydrin to the reaction vessel, is added the above alkylation mixture, 2200 g (23.78 eq.) of epichlorohydrin and 390 g of the methyl ether of propylene glycol (1-methoxy-2-hydroxypropane) as a solvent. Upon stirring at room temperature and atmospheric pressure to thoroughly mix the contents, the temperature is raised to 55° C. and the pressure is reduced to 105 mm Hg absolute. To the resulting solution is continuously added 188.7 g (2.358 eq.) of 50% aqueous sodium hydroxide solution at a constant rate over a period of 3 hours.

During the addition of the sodium hydroxide, the water is removed by codistilling with epichlorohydrin and solvent. The distillate is condensed, thereby forming two distinct phases, an aqueous phase (top) and an organic epichlorohydrin solvent phase (bottom). The organic phase is continuously returned to the reactor. Upon completion of the sodium hydroxide addition, the reaction mixture is maintained at a temperature of 55° C. and a pressure of 105 mm Hg absolute for an additional 30 minutes. The resulting glycidyl ether is distilled under full vacuum and at a temperature of up to 160° C. to generally remove all unreacted epichlorohydrin and 1-methoxy-2-hydroxy-propane. The molten glycidyl ether product is diluted to 50 percent resin concentration with a 75/25 methyl ethyl ketone/toluene solvent mixture. The mixture is heated to 85° C. for 2 hours with 0.7 g of 45% aqueous potassium hydroxide. The reaction mixture is further diluted to 20% resin concentration with a 75/25 methyl ethyl ketone/toluene solvent mixture, and the thus diluted product is washed with deionized water several times to remove salt. The organic phase from the water washes is placed on a rotary evaporator under a vacuum and at a temperature of 160° C. to remove the solvent. The resulting polyglycidyl ether has an epoxide content of 20.83% and contains 7.28% bromine, and has a Mettler softening point of 80° C. This epoxy resin is particularly suitable for use in electronic encapsulation formulations.

EXAMPLE 3

Advancement of Cresol Formaldehyde Epoxy Novolac Resin with 2,6-dibromo-3,5-dimethyl-4-hydroxybenzyl ether 500 g (2.5 eq.) of a cresol/formaldehyde epoxy novolac resin having a EEW of 183 and an average epoxide functionality of 6, a Kinematic viscosity of 125 centistokes ($125 \times 10^{-6}$ m$^2$/s) at 150° C. and containing 975 ppm total aliphatic chloride is dissolved in 500 g of a 75/25 percent by weight mixture of methyl ethyl ketone and toluene in a 2-liter flask equipped with thermowell, reflux condenser and stirrer. 83.6 g (0.287 eq.) of 2,6-dibromo-3,5-dimethyl-4-hydroxybenzyl ether is added to the epoxy resin solution and the resultant solution is heated to 85° C. with stirring. 2.1 g (1.2 eq. per eq. of total aliphatic chloride contained in the epoxy resin) of 45% aqueous potassium hydroxide is added all at once and the reaction mixture is maintained at 85° for 3 hours. The reaction mixture is diluted to 20% solids concentration with a 75/25 percent by weight methyl ethyl ketone/toluene solvent mixture, neutralized with carbon dioxide and washed with deionized water several times to remove the residual potassium chloride. The organic phase from the water washes is placed on a rotary evaporator under a full vacuum at 160° C. to remove the solvent. A yellow, solid resin having a Mettler softening point of 79° C., an EEW of 242, a viscosity of 227 centistokes ($227 \times 10^{-6}$ m$^2$/s) at 150° C. containing 642 ppm of total aliphatic chloride and 7.5% bromine is obtained.

EXAMPLE 4

Epoxidation of 2,6-dibromo-3,5-dimethyl-4-hydroxybenzyl ether and its Blending with Cresol Formaldehyde Epoxy Novolac (A) Epoxidation To a 2-liter reaction vessel equipped with a temperature and pressure control and indicating means, means for continuous addition of aqueous sodium hydroxide, a means for condensing and separating water from a codistillate mixture of water, solvent and epichlorohydrin and means for returning the solvent and epichlorohydrin to the reaction vessel is added 190.6 g (0.634 eq.) of 2,6-dibromo-3,5-dimethyl-4-hydroxybenzyl ether, 586.1 g (6.34 eq.) of epichlorohydrin and 103.4 g of the methyl ether of propylene glycol (1-methoxy-2-hydroxypropane) as a solvent. After stirring at room temperature ($\sim$25° C.) and atmospheric pressure to thoroughly mix the contents, the temperature is raised to 45° C. and the pressure is reduced to 65 mm Hg absolute. To the resulting solution is continuously added 50.7 g (0.634 eq.) of 50% aqueous sodium hydroxide solution at a constant rate over a period of 7 hours. During the addition of the sodium hydroxide, the water is removed by codistillation with epichlorohydrin and solvent. The distillate is condensed thereby forming two distinct phases, an aqueous phase (top) and an organic epichlorohydrin-solvent phase (bottom). The organic phase is continuously returned to the reactor. After completion of the sodium hydroxide addition, the reaction mixture is maintained at a temperature of 45° C. and a pressure of 65 mm Hg absolute for an additional one hour. The diglycidyl ether of 2,6-dibromo-3,5-dimethyl-4-hydroxybenzyl ether is not soluble in the organic solvent and precipitated from the reaction mixture. It is filtered from the reaction mixture and redissolved in methylene chloride. The methylene chloride solution is washed several times with deionized water to remove the residual sodium chloride. The organic phase from the water washes is placed in a vacuum oven under a vacuum at 160° C. to remove solvent completely. 210 g of yellowish white solid is obtained.

B. Blending 74 g (0.207 eq.) of the diglycidyl ether of 3,5-dimethyl-4-hydroxybenzyl ether prepared in A above and 346 g (1.725 eq.) of a cresol/formaldehyde epoxy novolac resin having a EEW of 191, an average epoxide functionality of 6, a Kinematic viscosity of 313 centistokes ($313 \cdot 10^{-6}$ m$^2$/s) at 150° C. and containing 622 ppm total aliphatic chloride are placed in a 1-liter flask on a rotary evaporator at 160° C. and a full vacuum until the two epoxy resins are completely mixed. The resultant mixture, 420 g of product, has an EEW of 211, a viscosity of 292 centistokes ($292 \times 10^{-6}$ m$^2$/s) at 150° C. and contains 7.5% bromine by weight.

EXAMPLE 5

Each of the products of Examples 2, 3 and 4 and a control resin are formulated into an electrical encapsulation formulation. The formulations are each cured at 175° C. for 4 hours. The encapsulation formulations are given in Table I.

TABLE I

| ENCAPSULATION FORMULATION | | | | |
|---|---|---|---|---|
| COMPONENT | A | B | C | D* |
| Epoxy Resin I, g | 21.4 | 34.4 | 27.5 | 168.8 |
| Epoxy Resin II Type/g | Ex. 2/ 171.7 | Ex. 3/ 166.7 | Ex. 4/ 166.7 | Control/ 26.3 |
| Curing Agent, g | 97.9 | 89.9 | 96.8 | 95.9 |
| triphenylphosphine, g | 2.0 | 2.0 | 2.0 | 2.0 |
| Mold release agent, g | 4.0 | 4.0 | 4.0 | 4.0 |
| Epoxy silane, g | 4.0 | 4.0 | 4.0 | 4.0 |
| Fused silica, g | 685.0 | 685.0 | 685.0 | 685.0 |
| Antimony oxide ($Sb_2O_3$), g | 10.0 | 10.0 | 10.0 | 10.0 |
| Carbon black, g | 4.0 | 4.0 | 4.0 | 4.0 |
| % Bromine in Formulation | 1.25 | 1.25 | 1.25 | 1.25 |

*Not an example of the present invention.

Epoxy Resin I is a cresol epoxy novolac resin having an epoxide equivalent weight (eq. wt.) of about 195 and a viscosity of about 420 centistokes at 150° C., commercially available from The Dow Chemical Company as QUATREX ™ 3430.

Epoxy Resin II is as listed.

The control epoxy resin is a solid, generally ortho-brominated epoxy resin having an epoxide equivalent weight (eq. wt.) of about 465, a viscosity of about 200 centistokes at 150° C., and a bromine content of 47.6% by weight, commercially available from The Dow Chemical Company as QUATREX ™ 6410.

The curing agent is a phenol-formaldehyde novolac resin with an average hydroxyl functionality of 6 and a phenolic hydroxyl equiv. wt. of about 104 commercially available from Schenectady Chemical as HRJ-2210.

The fused silica is GP-7I commercially available from Harbison-Walker Corporation.

The mold release agents are refined Montan waxes commercially available from Hoechst as OP; E.

The carbon black is Lampblack 101 commercially available from Degussa Corporation.

The epoxy silane is Z-6040 commercially available from Dow Corning Corporation.

FLAME RETARDANCY TEST

Above formulations all passed UL-94 VO flame retardancy test using castings of 1/16 inch thickness.

DEVICE RELIABILITY TEST

The device testing is determined by a highly accelerated stress test, which involves the following conditions: 121° C., 15 psig steam, and 25 volts bias. The device is a 14-pin LM 324 quad operational amplifier with a single passivation layer. The percentage of devices that fail as a function of time are given in the following table. Failure: each device is electrically tested for the necessary output voltage and currents as well as power dissipation. Any device which fails to meet these electrical parameters is considered a failure.

| | DEVICE RELIABILITY | | |
|---|---|---|---|
| Sample | % Device Failure[1] | | |
| Number | 400 hours | 600 hours | 800 hours |
| A | 3 | 7 | 28 |
| B | 5 | 10 | 40 |
| C | 2 | 6 | 21 |
| D* | 25 | 75 | 100 |

*Not an example of the present invention.
[1] % of a total of 100 devices tested with each formulation.

Thus, it can be seen that these stable meta-bromine-containing formulations give substantially better performances than the conventional systems.

What is claimed is:

1. A process for preparing phenolic hydroxyl-containing compounds represented by the formulas VII, VIII, IX, X or XI

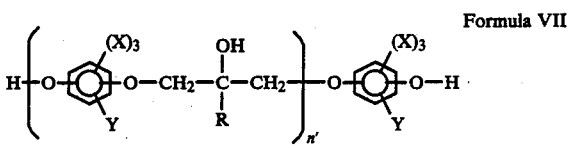

Formula VII

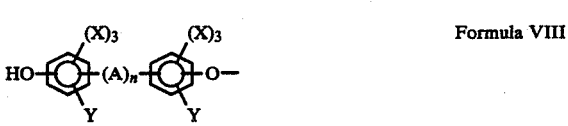

Formula VIII

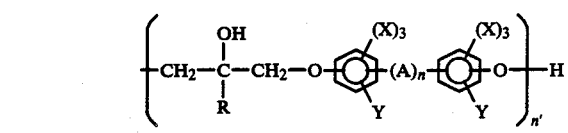

Formula IX

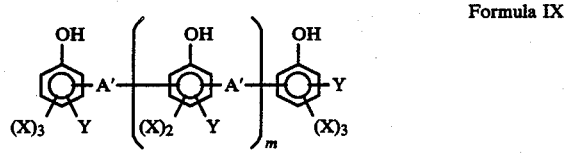

Formula X

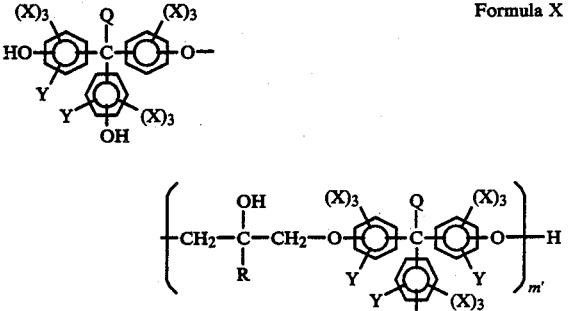

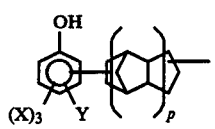

Formula XI

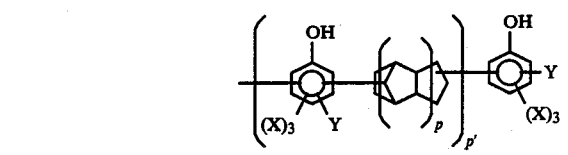

wherein each A is independently a divalent hydrocarbyl group having from 1 to about 12 carbon atoms; each A' is independently a divalent hydrocarbyl group having from 1 to about 10 carbon atoms; each Q is independently hydrogen or an alkyl group having from 1 to about 4 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms or a halogen atom; each Y is independently hydrogen or a group represented by the following formula XII wherein R' is an alkyl group having from 1 to about 10 carbon atoms with the proviso that at least one Y group is a group represented by formula XII;

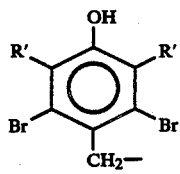

Formula XII m has an average value from about 0.01 to about 8; m' has an average value from zero to about 10; n has a value of zero or 1; n' has an average value from about zero to about 3; each p has a value from zero to about 10; and each p' has an average value from zero to about 8; which process comprises reacting (A) one or more 2,6-dibromo-3,5-dialkyl-4-hydroxybenzyl ethers represented by the following formula I

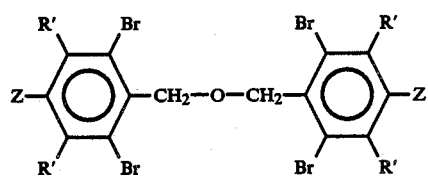

Formula I wherein each R' is independently an alkyl group having from 1 to about 10 carbon atoms and each Z is a hydroxyl group; with (B) one or more phenolic hydroxyl containing compounds having an average of more than one phenolic hydroxyl group per molecule represented by the following formulas II, III, IV, V or VI

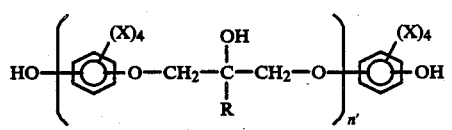

Formula II

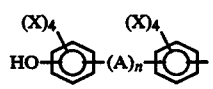

Formula III

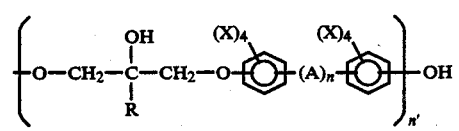

Formula IV

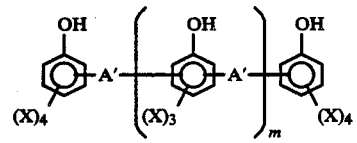

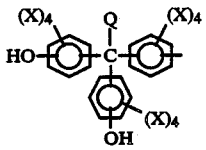

Formula V

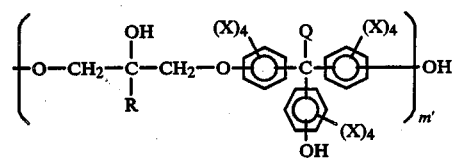

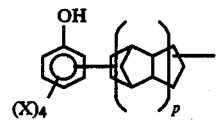

Formula VI wherein each A is independently a divalent hydrocarbyl group having from 1 to about 12 carbon atoms; each A' is independently a divalent hydrocarbyl group having from 1 to about 10 carbon atoms; each Q is independently hydrogen or an alkyl group having from 1 to about 4 carbon atoms; each R is independently hydrogen or an alkyl group having from 1 to about 3 carbon atoms; and each X is independently hydrogen, a hydrocarbyl or hydrocarbyloxy group having from 1 to about 12 carbon atoms or a halogen atom; and wherein components (A) and (B) are employed in quantities which provide a ratio of phenolic hydroxyl groups from 2,6-dibromo-3,5-dialkyl-4-hydroxybenzyl ether to aromatic rings from the phenolic hydroxyl containing compound of from about 0.05:1 to about 0.5:1.

2. A process of claim 1 wherein
(a) in component (A) each R' is independently an alkyl group having from 1 to about 6 carbon atoms;
(b) in component (B) each A is independently a divalent hydrocarbyl group having from 1 to about 6 carbon atoms; each A' is independently a divalent hydrocarbyl group having from 1 to about 4 carbon atoms; each R is hydrogen; each X is independently hydrogen, a hydrocarbyl or hydrocarbyloxy group having from 1 to about 6 carbon atoms or chlorine or bromine; Z is a hydroxyl group; m has an average value from about 1 to about 6; m' has an average value from zero to about 6; n has a value of 1; n' has an average value from zero to about 2; each p has a value from zero to about 6; and each p' has an average value from about 1 to about 6; and
(c) components (A) and (B) are employed in quantities which provide a ratio of phenolic hydroxyl groups from 2,6-dibromo-3,5-dialkyl-4-hydroxybenzyl ether to aromatic rings from the phenolic hydroxyl containing compound of from about 0.05:1 to about 0.3:1.

3. A process of claim 2 wherein (a) in component (A) each R' is independently an alkyl group having from 1 to about 3 carbon atoms;

(b) in component (B) each A is independently a divalent hydrocarbyl group having from 1 to about 4 carbon atoms; each A' is independently a divalent hydrocarbyl group having from 1 to about 2 carbon atoms; each Q is hydrogen; each X is independently hydrogen, a hydrocarbyl or hydrocarbyloxy group having from 1 to about 4 carbon atoms or chlorine or bromine; Z is a hydroxyl group; m has an average value from about 2 to about 4; m' has an average value from zero to about 3; n' has an average value from zero to about 1; each p has a value from zero to about 3; and each p' has an average value from about 2 to about 4; and (c) components (A) and (B) are employed in quantities which provide a ratio of phenolic hydroxyl groups from 2,6-dibromo-3,5-dialkyl-4-hydroxybenzyl ether to aromatic rings from the phenolic hydroxyl containing compound of from about 0.05:1 to about 0.2:1.

4. A process of claim 3 wherein
(a) component A is 2,6-dibromo-3,5-dimethyl-4-hydroxybenzyl ether; and
(b) component (B) is represented by formulas II or III.

5. A product produced by the process of claim 1, 2, 3 or 4.

6. A compound or mixture of compounds represented by the following formulas VII, VIII, IX, X or XI

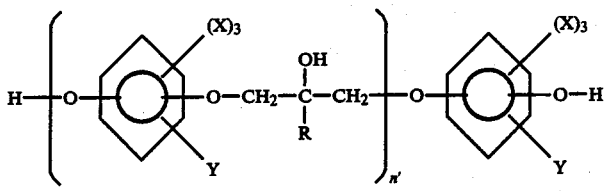

Formula VII

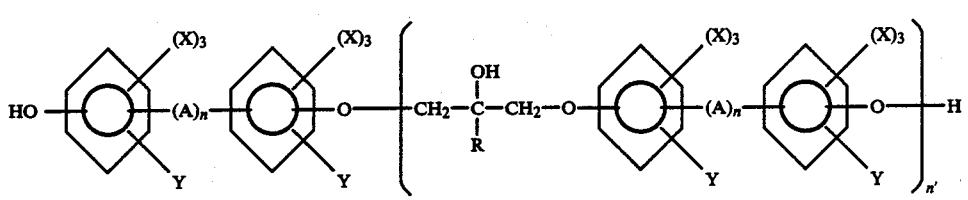

Formula VIII

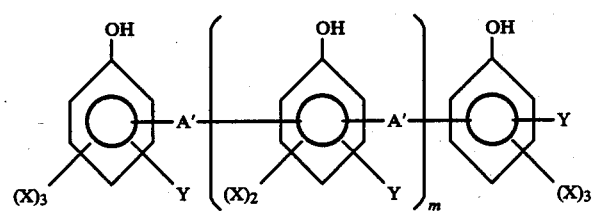

Formula IX

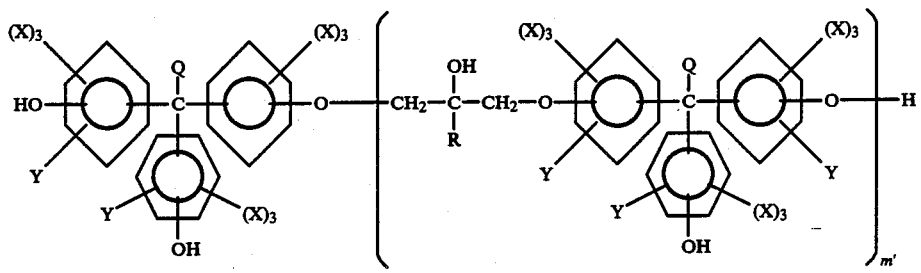

Formula X

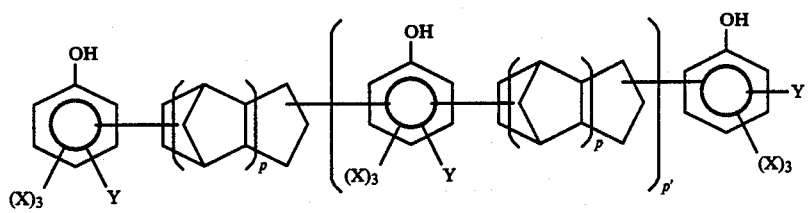

Formula XI wherein each A is independently a divalent hydrocarbyl group having from 1 to about 12 carbon atoms; each A' is independently a divalent hydrocarbyl group having from 1 to about 10 carbon atoms; each Q is independently hydrogen or an alkyl group having from 1 to about 4 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms or a halogen atom; each Y is independently hydrogen or a group represented by the following formula XII wherein R' is an alkyl group having from 1 to about 10 carbon atoms with the proviso that at least one Y group is a group represented by formula XII;

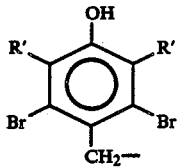

Formula XII m has an average value from about 0.01 to about 8; m' has an average value from zero to about 10; n has a value of zero or 1; n' has an average value from about zero to about 3; each p has a value from zero to about 10; and each p' has an average value from zero to about 8.

7. A compound or mixture of compounds of claim 6 wherein each A is independently a divalent hydrocarbyl group having from 1 to about 6 carbon atoms; each A' is independently a divalent hydrocarbyl group having from 1 to about 4 carbon atoms; each R is hydrogen; each X is independently hydrogen, a hydrocarbyl or hydrocarbyloxy group having from 1 to about 6 carbon atoms or a halogen atom; R' is an alkyl group having from 1 to about 6 carbon atoms; m has an average value from about 2 to about 4; m' has an average value from zero to about 6; n has a value of 1; n' has an average value from zero to about 2; each p has a value from zero to about 6; and each p' has an average value from 2 to about 4.

8. A compound or mixture of compounds of claim 7 wherein each A is independently a divalent hydrocarbyl group having from 1 to about 4 carbon atoms; each A' is independently a divalent hydrocarbyl group having from 1 to about 2 carbon atoms; each Q is independently hydrogen; each R is hydrogen; each X is independently hydrogen, a hydrocarbyl or hydrocarbyloxy group having from 1 to about 6 carbon atoms or a halogen atom; R' is an alkyl group having from 1 to about 3 carbon atoms; m has an average value from about 1 to about 6; m' has an average value from azero to about 3; n has a value of 1; n' has an average value from zero to about 1; each p has a value from zero to about 3; and each p' has an average value from 1 to about 6.

* * * * *

UNITED STATES PATENT AND TRADEMARK OFFICE
CERTIFICATE OF CORRECTION

PATENT NO. : 4,892,925
DATED : January 9, 1990
INVENTOR(S) : Chun S. Wang, et al.

It is certified that error appears in the above-identified patent and that said Letters Patent is hereby corrected as shown below:

Column 11, Formula XVII; change

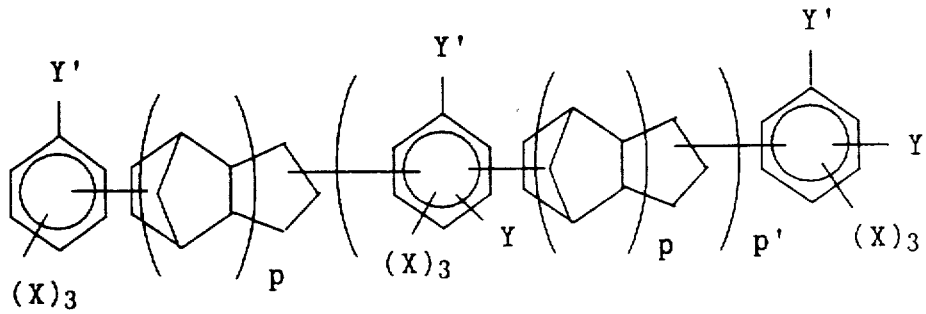

UNITED STATES PATENT AND TRADEMARK OFFICE
CERTIFICATE OF CORRECTION

PATENT NO. : 4,892,925

DATED : January 9, 1990

INVENTOR(S) : Chun S. Wang, et al

It is certified that error appears in the above-identified patent and that said Letters Patent is hereby corrected as shown below:

to read

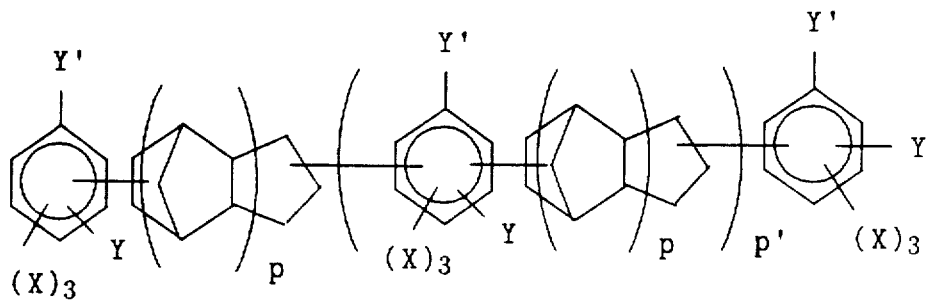

Signed and Sealed this

Tenth Day of March, 1992

Attest:

HARRY F. MANBECK, JR.

Attesting Officer     Commissioner of Patents and Trademarks